United States Patent

Nagel

[11] Patent Number: 5,977,131
[45] Date of Patent: Nov. 2, 1999

[54] AZAINDOLE-ETHYLAMINE DERIVATIVES AS NICOTINIC ACETYLCHOLINE RECEPTOR BINDING AGENTS

[75] Inventor: Arhur A. Nagel, Gales Ferry, Conn.

[73] Assignee: Pfizer Inc., New York, N.Y.

[21] Appl. No.: 09/052,172

[22] Filed: Mar. 31, 1998

Related U.S. Application Data

[60] Provisional application No. 60/043,417, Apr. 9, 1997.

[51] Int. Cl.$^6$ .................................................. A01N 43/42
[52] U.S. Cl. .......................................... 514/300; 546/113
[58] Field of Search ............................. 514/300; 546/113

[56] References Cited

U.S. PATENT DOCUMENTS

| | | | |
|---|---|---|---|
| 3,362,956 | 1/1968 | Archer | 260/268 |
| 5,436,128 | 7/1995 | Harpold et al. | 435/6 |
| 5,547,960 | 8/1996 | Kozikowski et al. | 514/295 |
| 5,547,965 | 8/1996 | Kruger et al. | 514/342 |
| 5,583,140 | 12/1996 | Bencherif et al. | 514/299 |

OTHER PUBLICATIONS

British Medical Bulletin (1986) vol. 42, No. 1, pp. 63–69, Elaine K. Perry, "The Cholinergic Hypothesis—Ten Years On".

Science, vol. 217, Jul. 30, 1982, Raymond T. Bartus, et al, "The Cholinergic Hypothesis of Geriatric Memory Dysfunction".

The Lancet, Mar. 26, 1971, P. White, et al, "Neocortical Cholinergic Neurons In Elderly People".

Journal; Robison; Robison; JACSAT; J. Amer. Chem. Soc.; 78; 1956; 1247, 1249.

Blanche et al., "Application of the Mercuric Acetate–edetic Acid Oxidation Method to the Synthesis of 11–aza–1,2,3,4, 5,6,7,12b–octahydroindolo[2,3–a]quinolizines", Heterocycles, vol. 45, No. 1, Feb. 26, 1997, pp. 57–69.

Journal; Robinson; JACSAT; J. Amer. Chem. Soc.; 78; 1956; 1247, 1249.

La Manna et al., "Synthesis of 7–azatryptamines", Boll. Chim. Farm. 112(1), 12–21, 1973, see abstract only.

Yakhontov et al., "Azaindole derivatives. XLVII. Synthesis and pharmacological study of 3–aminoalkyl derivatives of azaindoles", Khim.–Farm. Zh. 8(11), 5–9, 1974, see abstract only.

*Primary Examiner*—Dwayne C. Jones
*Attorney, Agent, or Firm*—Peter C. Richardson; Gregg C. Benson; Mervin E. Brokke

[57] ABSTRACT

Compounds of formula I are useful in treatment of conditions associated with depletion of nicotine receptors in mammals.

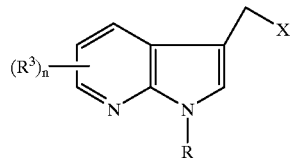

(I)

6 Claims, No Drawings

AZAINDOLE-ETHYLAMINE DERIVATIVES AS NICOTINIC ACETYLCHOLINE RECEPTOR BINDING AGENTS

This application claims priority on provisional application 60/043,417, filed Apr. 9, 1997.

BACKGROUND OF THE INVENTION

This invention relates to heterocyclic compounds. More particularly it relates to azaindole amine compounds of the formula I below. Compounds of formula I are useful in the treatment of addictive disorders such as the use of tobacco or other nicotine containing products. These compounds are also useful in the treatment of neurological and mental disorders such as senile dementia of the Alzheimer's type, Parkinson's disease, attention hyperactivity disorder, anxiety, obesity, Tourette's Syndrome and ulcerative colitis.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, Huntington's chorea, dyskinesia, hyperkinesia, mania, attention deficit disorder, anxiety, dyslexia, schizophrenia and Tourette's syndrome.

Senile dementia of the Alzheimers type (SDAT) is a debilitating neurodegenerative disease, mainly afflicting the elderly; characterized by a progressive intellectual and personality decline, as well as a loss of memory, perception, reasoning, orientation and judgment. One feature of the disease is an observed decline in the function of cholinergic systems, and specifically, a severe depletion of cholinergic neurons (i.e., neurons that release acetylcholine, which is believed to be a neurotransmitter involved in learning and memory mechanisms). See, Jones, et al., *Intem. J. Neurosci.*, Vol 50, p. 147 (1990); Perry, *Br Med. Bull.*, Vol. 42, p. 63 (1986) and Sitaram, et al., *Science*, Vol. 201, p. 274 (1978). It has been observed that nicotinic acetylcholine receptors, which bind nicotine and other nicotinic agonists with high affinity, are depleted during the progression of SDAT. See. Giacobini, *J. Neurosci. Res.*, Vol. 27, p. 548 (1990); and Baron, *Neurology*, Vol. 36, p. 1490 (1986). As such, it would seem desirable to provide therapeutic compounds which either directly activate nicotinic receptors in place of acetylcholine or act to minimize the loss of those nicotinic receptors.

The cholinergic hypothesis (see Bartus, et al. *Science*, 217 408 1982) states that the enzyme choline acetyltransferase is depleted in SDAT. This prevents the conversion of choline to acetylcholine. The post-synaptic receptors for the most part remain unimpaired. A chemical replacement for acetylcholine, i.e., nicotinic or muscarine agonist will be effective only if the receptor remains intact.

Certain attempts have been made to treat SDAT. For example, nicotine has been suggested to possess an ability to activate nicotinic cholinergic receptors upon acute administration, and to elicit an increase in the number of such receptors upon chronic administration to animals. See, Rowell, *Adv. Behav. biol.*, Vol. 3 1, p. 191 (1987); and Marks, *J. Pharmacol. Exp. 7her*, Vol. 226, p. 817 (1983). It also has been proposed that nicotine can act directly to elicit the release of acetylcholine in brain tissue, to improve cognitive functions, and to enhance attention. See, Rowell, et al., *J. Neurochem.*, Vol. 43, p.1593 (1984); Sherwood, Human *Psychopharm.*, Vol. 8, pp. 155–184 (1993); Hodges, et al., *Bio. of Nic., Edit. by Lippiello, et al.,* p.157 (1991); Sahakian, et al., *Br. J. Psych.*, Vol. 154, p. 797 (1989); and U.S. Pat. No. 4,965,074 to Leeson and U.S. Pat. No. 5,242,935 to Lippiello et al. Other methods for treating SDAT have been proposed, including U.S. Pat. No. 5,212, 188 to Caldwell et al. and U.S. Pat. No. 5,227,391 to Caldwell et al. and European Patent Application No. 588, 917.

Parkinson's disease (PD) is a debilitating neurodegenerative disease, presently of unknown etiology, characterized by tremor and muscular rigidity. A feature of the disease appears to involve the degeneration of dopaminergic neurons (i.e., which secrete dopamine). One symptom of the disease has been observed to be a concomitant loss of nicotinic receptors which are associated with such dopaminergic neurons, and which are believed to modulate the process of dopamine secretion. See, Rinne, et al., *Brain Res.*, Vol. 54, pp. 167–170 (1991) and Clark, et al., *Br J. Pharm.*, Vol. 85, pp. 827–835 (1985). It also has been proposed that nicotine can ameliorate the symptoms of PD. See, Smith et al., *Rev. Neurosci.*, Vol. 3(I), pp. 25–43 (1982).

Tourette's syndrome (TS) is an autosomal dominant neuropsychiatric disorder characterized by a range of neurological and behavioral symptoms. Typical symptoms include (i) the onset of the disorder before the age of 21 years, (ii) multiple motor and phonic tics although not necessarily concurrently, (iii) variance in the clinical phenomenology of the tics, and (iv) occurrence of quasi daily tics throughout a period of time exceeding a year. Motor tics generally include eye blinking, head jerking, shoulder shrugging and facial grimacing; while phonic or vocal tics include throat clearing, sniffling, yelping, tongue clicking and uttering words out of context. The pathophysiology of TS presently is unknown, however it is believed that neurotransmission dysfunction is implicated with the disorder. See, Calderon-Gonzalez et al., *Intem. Pediat.*, Vol. 8(2), pp. 176–188 (1993) and *Oxford Textbook of Medicine*, Eds. Weatherall et al., Chapter 21.218 (1987).

It has been proposed that nicotine pharmacology is beneficial in suppressing the symptoms associated with TS. See, Devor et al., *The Lancet*, Vol. 8670, p. 1046 (1989); Jarvik, *British J. of Addiction*, Vol. 86, pp. 571–575 (1991); McConville et al., *Am. J. Psychiatry.*, Vol.148 (6), pp. 793–794 (1991); Newhouse et al., *Brit. J, Addic.*, Vol. 86, pp. 521–526 (1991); McConville et al., *Biol. Psychiatry*, Vol. 31, pp. 832–840 (1992); and Sanberg et al., *Proceedings from Intl. Syrup. Nic.*, S39 (1994).

Attention deficit disorder (ADD) is a disorder which affects mainly children, although ADD can affect adolescents and adults. See, Vinson, *Arch. Fam. Med.*, Vol. 3(5), pp. 445–451 (1994); Hechtman, *J. Psychiatry Neurosci.*, Vol. 19 (3), pp. 193–201 (1994); Faraone et al., *Biol. Psychiatry.*, Vol. 35(6), pp. 398–402 (1994) and Malone et al., *J. Child Neurol*, Vol. 9(2), pp. 181–189 (1994). Subjects suffering from the disorder typically have difficulty concentrating, listening, learning and completing tasks; and are restless, fidgety, impulsive and easily distracted. Attention deficit disorder with hyperactivity (ADHD) Includes the symptoms of ADD as well as a high level of activity (e.g., restlessness and movement). It has been reported that administration of nicotine to an individual improves that individual's selective and sustained attention. See, Warburton et al., *Cholinergic control of cognitive resources, Neuropsychobiology*, Eds. Mendlewicz, et al., pp 43–46 (1993).

Schizophrenia is characterized by psychotic symptoms including delusions, catatonic behavior and prominent hallucinations, and ultimately results in a profound decline in the psychosocial affect of the subject suffering therefrom. Neuroleptics used to treat schizophrenia are believed to be effective as a result of interaction thereof with the dopaminergic pathways of the CNS. In addition, a dopaminergic dysfunction possessed by individuals suffering from schizophrenia has been proposed. See, Lieberman et al., *Schizophr. Bull.*, Vol. 19, pp. 371–429 (1993) and Glassman, *Amer. J. Psychiatry.*, Vol. 150, pp. 546–553 (1993). Nicotine has been proposed as being effective in effecting neurotransmitter dysfunction associated with schizophrenia. See, Merriam et al., *Psychiatr. Annals*, Vol. 23, pp. 171–178 (1993) and Adler et al., *Biol. Psychiatry*, Vol. 32, pp. 607–616 (1992).

Nicotine has been proposed to have a number of pharmacological effects. Certain of those effects may be related to effects upon neurotransmitter release. See, for example, Sjak-shie et al., *Brain Res.*, Vol. 624, pp. 295–298 (1993), where neuroprotective effects of nicotine are proposed. Release of acetylcholine and dopamine by neurons upon administration of nicotine has been reported by Rowell et al., *J. Neurochem.*, Vol.43, pp. 1593–1598 (1984); Rapier et al., *J. Neurochem.*, Vol. 50, pp. 1123–1130 (1988); Sandor et al., *Brain Res.*, Vol. 567, pp. 313–316 (1991) and Vizi, *Br J. Pharmacol.*, Vol. 47, pp. 765–777 (1973). Release of norepinephrine by neurons upon administration of nicotine has been reported by Hall et al., *Biochem. Pharmacol.*, Vol. 21, pp. 1829–1838 (1972). Release of serotonin by neurons upon administration of nicotine has been reported by Hery et al., *Arch. Int, Pharmacodyn. Ther.*, Vol. 296, pp. 91–97 (1977). Release of glutamate by neurons upon administration of nicotine has been reported by Toth et al., *Neurochom Res.*, Vol. 17,pp. 265–271 (1992). Therefore, it would be desirable to provide a pharmaceutical composition containing an active ingredient having nicotinic pharmacology, which pharmaceutical composition is capable of eliciting neurotransmitter release within a subject in order to prevent or treat a neurological disorder. In addition, nicotine reportedly potentiates the pharmacological behavior of certain pharmaceutical compositions used for the treatment of certain Central Nervous System (CNS) disorders. See, Sanberg et al., *Pharmacol. Biochem. & Behavior*, Vol. 46, pp. 303–307 (1993); Harsing et al., *J. Neurochem.*, Vol. 59, pp. 48–54 (1993) and Hughes, *Proceedings from Intl. Symp. Nic.*, S40 (1994). Furthermore, various other beneficial pharmacological effects of nicotine have been proposed. See, Decina et al., *Biol. Psychiatry*, Vol. 28, pp. 502–508 (1990); Wagner et al., *Pharmacopsychiatry*, Vol. 21, pp. 301–303 (1988); Pomerieau at al., *Addictive Behaviors*, Vol. 9, p. 265 (1984); Onaivi et al., *Life Sci.*, Vol. 54(3), pp. 193–202 (1994) and Hamon, *Trends in Pharmacol*, Res., Vol. 15, pp. 36–39.

It would be desirable to provide a useful method for the prevention and treatment of a CNS disorder by administering a nicotinic compound to a patient susceptible to or suffering from such a disorder. It would be highly beneficial to provide individuals suffering from certain CNS disorders with interruption of the symptoms of those diseases by the administration of a pharmaceutical composition which has nicotinic pharmacology and which has a beneficial effect upon the functioning of the CNS, but which does not provide any significant associated side effects (e.g., increased heart rate and blood pressure) attendant with interaction of that compound with cardiovascular sites. It would be highly desirable to provide a pharmaceutical composition incorporating a compound which interacts with nicotinic receptors which have the potential to affect the functioning of the CNS, but which does not significantly affect those receptors which have the potential to induce undesirable side effects (e.g., appreciable pressor cardiovascular effects and appreciable activity at skeletal muscle sites).

Substances which can deliver pharmacologically relevant amounts of nicotine to the central nervous system are among the most abused substances known. These include, but not are not limited to tobacco cigarettes, and "chewing tobacco" (see J. E. Henningfield, Ph.D, *New England journal of Med.*, 1196, 1995). Cigarette smoking has been tied to increased risk for lung cancer, emphysema and heart disease and it is estimated 400,000 people will die in 1995 from the combined effects of nicotine abuse in the United States (see J. A. Califano, Jr., *New England Journal of Med.* 1214, 1995). Nicotine is a highly addicting drug with 40% of those who try smoking later becoming physically dependent upon it Attempts to quit the use of nicotine, such as in smoking, have been largely ineffective with >80% of such attempts ending in failure. Most attempts to quit end in failure in the first week due to intense withdrawal and craving symptoms. An effective therapy should prevent withdrawal symptoms, relieve craving and, simultaneously, antagonize the reinforcing effects of nicotine obtained through smoking. Currently, few therapies are available for smoking cessation and most involve replacement of cigarettes with nicotine in the form of a patch or gum. A high rate of relapse and low overall success in ending nicotine use is evidence of the need for additional and more effective therapies for treatment of nicotine addiction than the nicotine patch or gum.

Pharmaceutical compositions employed for the treatment of chronic nicotinism and addiction to nicotine can be divided into two groups. The first covers salts of silver, iron and copper. These substances are employed to develop a negative reflex to smoking usually in the form of a solution, or by incorporation in chewing gum compositions. The resultant reflex is based on the appearance of a strong unpleasant taste in the mouth during smoking after a preliminary rinsing of the mouth cavity with solutions of salts, or after the use of a chewing gum containing such salts (See Nasirov et al. "Anabasine Hydrochloride—New Antismoking Agent", *Chemico-Pharmaceutical Journal*, vol. XII, 1978, No. 2, 149–152).

The second group of agents that are used for the suppression of nicotine addition comprises substances of an alkaloidal nature, such as 1,2,3,4,5,6-hexahydro-1,5-methanopyrido[1,2-a][1,5]diazocin-8-one (hereafter 'cytisine), lobeline and anabasine hydrochloride, possessing an effect on H-cholinoreactive systems of the organism similar to that of nicotine. The mechanism of their effect is due to their structural similarity with nicotine and the possible "competitive" antagonism between these alkaloids and nicotine (F. R. Khalikova, S. H. Nasirov, "On pharmacology of the Alkaloid Anabasine and some Polymeric and Copolymeric Derivatives Thereof", in Coll. "Pharmacology of Vegetable Compounds", Proceedings of Tashkent University, 457, 1973, 5–16).

U.S. Pat. No. 4,971,079 describes a composition comprising a biologically resorbable polymer containing a cation exchange group modified by an antinicotine action alkaloid, such as anabasine or cytsine, and a gum containing same. However, it has been found that the potency of cytisine is not high due to its inability to penetrate the brain barrier. (Reavill, C. et al., *Behavioural and Pharmacokinetic Studies On Nivotine, Cytisine and Lobeline, Neuropharmacology*, 29, 619–624 (1990)). Labadie L.C. ((*Peut-on supprimer les facteurs de risque on bronchopatie chronique et en particular le tabac, Mediater, med.*, 1976, 4, No. 112, 97, 99)) describes the use of leaves of other night-shade plants, such as potato, tomato, eggplant and digitalis as tobacco substitutes.

One of the most successful approaches to date in reducing the incidence of smoking relies upon nicotine containing chewing gum which is designed to reduce smoking withdrawal symptoms. The reported success rate, while still relatively low, is approximately twice that of the other methods which have heretofore been employed. (See *British Medical Journal*, 286, (1983)).

The use of the nicotine gum suffers from several problems including bad taste, destruction of dental appliances and gastrointestinal discomfort thereby reducing their use to suppress nicotine addiction. In addition, it has been found that the nicotine containing gum does not completely satisfy the craving that most smokers experience for nicotine and often nicotine gum becomes addictive to the patient A simulated smoking device which uses a source of vaporizable nicotine is claimed in U.S. Pat. No. 4,284,089. While the cigarette itself is non-combustible it delivers a nicotine-containing vapor which may not raise the nicotine level in the blood sufficiently to satisfy a smoker. Thus, it has not been shown to satisfy the desire for a certain nicotine level in the blood to which many smokers have become accustomed and, even more so, upon which many smokers have become dependent in addition, the simulated smoking devices of the type taught in U.S. Pat. No. 4,284,089 also suffer from the bad taste of a substantial amount of nicotine introduced into the oral cavity. More importantly, this nicotine does not penetrate into the lungs for stimulating and providing that sensation normally provided by nicotine and to which the smoker has become accustomed.

The current first line therapy for smoking cessation, as described in U.S. Pat. No. 5,016,652 describes a transdermal patch which is useful for the controlled delivery of nicotine to the bloodstream of the user thereby reducing the incidence of smoking. Clinical trials have shown that abstinence rates (with the nicotine patch) of 30 to 40% can be achieved during the first six weeks of application (K. J. Palmer, M. M. Buckley, D. Faulds; *Drugs* 44(3) 498–529, (1992) compared with 4 to 21% with a placebo. However, long term abstinence rates (>6 months) are considerably lower; falling to between 11–18%. Thus, a more effective therapy which will afford a greater percentage of smokers who are able to quit is dearly needed.

A copending application (Attorney's Docket No. PC9582), assigned to the assignee of this application and incorporated herein in its entirety, refers to pyridine-fused heterocyclic compounds which are useful in the treatment of addictive disorders such as the use of tobacco or other nicotine containing products or in the treatment of neurological and mental disorders related to a decrease in cholinergic function.

Copending application (Attorney's Docket No. PC9728), assigned to the assignee of this application and incorporated herein in its entirety, refers to 7-aza bicycloheptanes which are useful in the treatment of addictive disorders such as the use of tobacco or other nicotine containing products or in the treatment of neurological and mental disorders related to a decrease in cholinergic function.

Copending application (Attorney's Docket No. PC9572) assigned to the assignee of this application and incorporated herein by reference describes certain (N-(pyridinylmethyl)-heterocylic)ylideneamine compounds as nicotinic acetylcholine receptor binding agents.

SUMMARY OF THE INVENTION

This invention relates to a compound of the formula

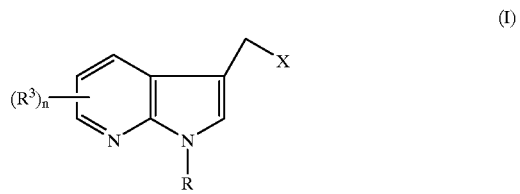

wherein X is:

a) —CH$_2$NR$^1$R$^2$,

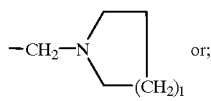

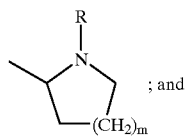

R, R$^1$, and R$^2$ are independently selected from hydrogen and C$_1$–C$_6$ alkyl;

R$^3$ is selected from hydrogen, halogen and C$_1$–C$_6$ alkyl;

l is an integer from 0–4;

m is an integer from 0–4; and n is an integer from 0–2; and pharmaceutically acceptable salts thereof.

Preferred compounds of Formula I are:

[2-(6-chloro-1H-pyrrolo[2,3-b]pyridin-3yl)ethyl]-dimethylamine;

[2-(6-chloro-1H-pyrrolo[2,3-b]pyridin-3yl)ethyl]-methylamine;

3-pyrrolidin-2-ylmethyl-1H-pyrrolo[2,3-b]pyridine;

3-(1-methyl-pyrrolidin-2-ylmethyl)-1-H-pyrrolo[2,3-b]pyridine;

dimethyl-[2-(1H-pyrrolo[2,3-b]pyridin-3-yl)-ethyl]-amine;

methyl-[2-(1H-pyrrolo[2,3-b]pyridin-3-yl)-ethyl]-amine;

2-(1H-pyrrolo[2,3-b]pyridin-3-yl-ethylamine; and 3-(2-piperidin-1-yl-ethyl-1H-pyrrolo[2,3-b]pyridine.

In another aspect, this invention provides a method for treating a disease or condition of the brain associated with depletion of nicotinic receptors in a patient in need thereof comprising administering to said patient an effective amount of a compound of formula I above or a pharmaceutically acceptable salt or prodrug thereof.

In another aspect this invention provides a pharmaceutical composition comprising a compound of formula I and a pharmaceutically inert carrier.

The present invention also relates to all radiolabelled forms of the compounds of formula I comprising at least one radiolabel preferably selected from $^3H$, $^{11}C$ and $^{14}C$. Such radiolabelled compounds are useful as research and diagnostic tools in metabolism pharmacokinetic studies and in binding assays in both animals and man.

In addition, the present invention relates to pharmaceutical compositions for use in reducing nicotine addiction in a mammal comprising an amount of a compound of the formula (I), above, or a pharmaceutially acceptable salt or prodrug thereof, effective in reducing nicotine addiction and a pharmaceutically acceptable carrier.

Yet another aspect of the present invention relates to compounds of formula I wherein said pharmaceutically acceptable add addition salts are the salts of acids selected from the group comprising hydrochoric acid, p-toluenesulfonic acid, fumaric acid, citric acid, succinic acid, salicylic acid, oxalic acid, hydrobromic acid, phosphoric acid, methanesulfonic acid, tartaric acid, di-p-toluoyl tartaric acid, and mandelic acid.

Another embodiment of present invention relates to a method for treating addictive disorders and neurological or mental disorders in a mammal which comprises administering to said mammal an amount of a compound of the formula I effective in treating addictive disorders and neurological or mental disorders.

DETAILED DESCRIPTION OF THE INVENTION

Compounds of the present invention illustrated in formula I above are easily prepared from readily available starting material. Sustituted 1H-pyrrolo-[2,3-b]pyridines are available from commercial sources or are known in the chemical literature. See, for example, (*Synthesis,* 1992, 7, 661–663); (*Arch. Pharm.* 1991, 324, 433–437); and (*J. Am. Chem. Soc.* 1955, 77, 457–459).

In a general procedure illustrated below, an optionally substituted 1H-pyrrolo[2,3-b]pyridine is reacted with a substituted acid chloride such as chloroacetyl chloride in a reaction-inert solvent and in the presence of an acid catalyst to produce 2-chloro-1-(1H-pyrrolo[2,3-b]pyridin-3yl)-ethanones.

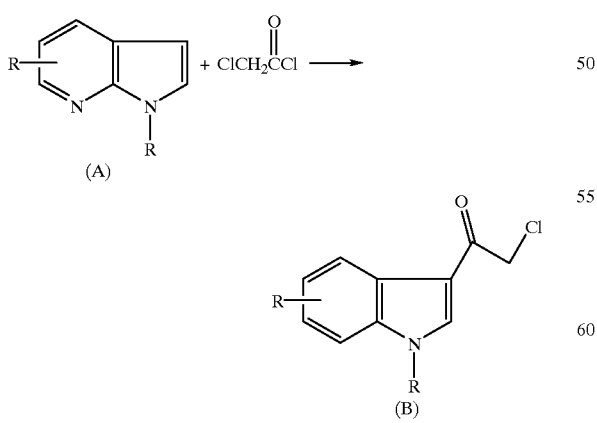

Compound B is reduced to the corresponding chloroethyl compound, preferably with trimethylsilane in trifluoroacetic acid solvent and the product is isolated by standard procedures to yield compound (C)

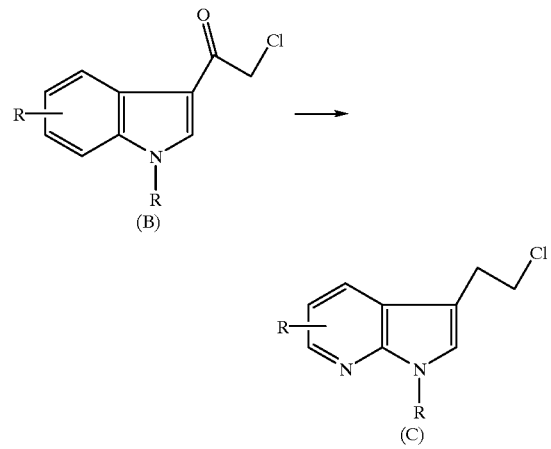

Conversion of compound (C) to the corresponding amine derivative (compound D) is easily accomplished by reaction with the selected amine in a reaction inert solvent with an iodide catalyst. An alternative sequence is to prepare and isolate the intermediate iodo compound (D) and subsequently converted to compound (E) with the appropriate amine.

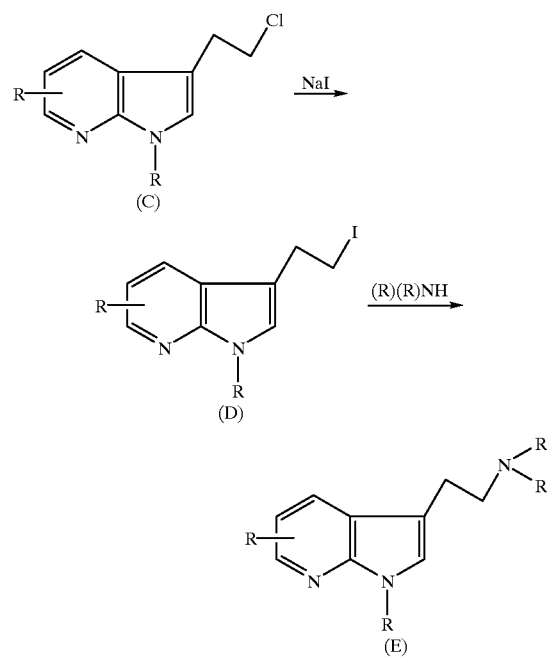

In another aspect, pyrrolo[2,3-b]pyridine-3-carbaldehydes are employed as starting materials for compounds of the invention.

Thus, compound (F) below is reacted with an appropriate nitro ester in the presence of ammonium acetate in a reaction inert solvent to produce an alkenoic ester, compound (G) which is further reacted with sodium borohydride to remove the double bond and form compound (H).

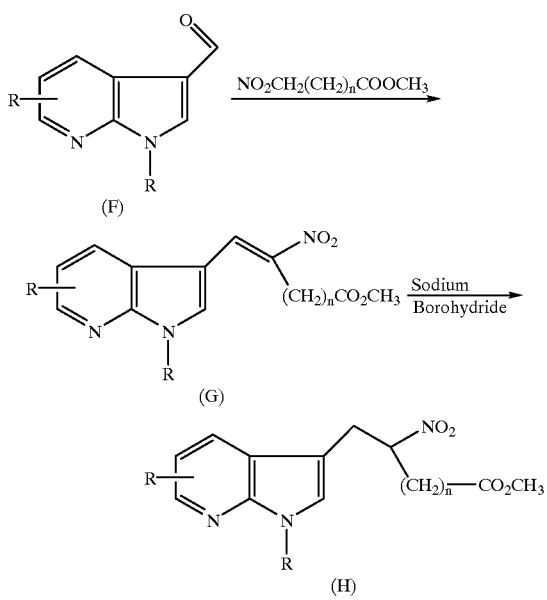

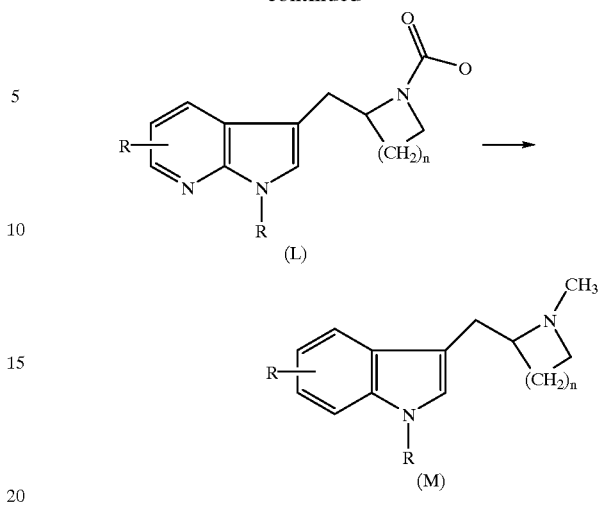

Compound (H) is then reduced with a suitable reducing agent such as Raney nickel and hydrogen to form the corresponding amine compound (I) which is converted under basic conditions to the cyclic amide (J).

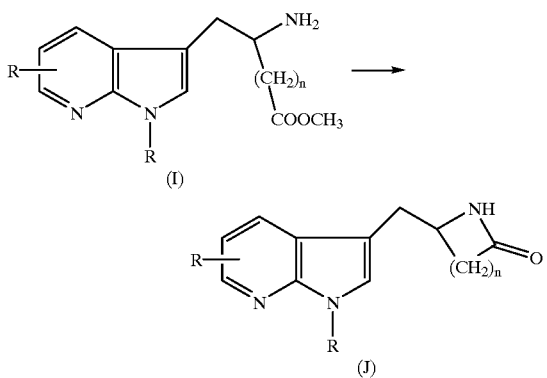

The cyclic amide, compound (J) is then reduced to the cyclic amine (K) with a strong reducing agent, for example lithium aluminum hydride. The amine (K) may then be methylated in a two step process to form the final product compound (M). First the t-butylester is prepared from compound (K) with di-tert-butyl-dicarbonate to form the amide (L). Reduction of (L) with lithium aluminum hydride yields the desired N-methyl cyclic amino compound (M).

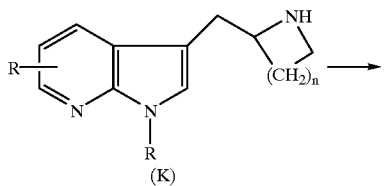

The salts of the compound of formula I are prepared by treating the free base forms thereof with appropriate acids under the general conditions known to the art. For instance, they may be prepared by contacting the compound (group) of the formula I with an appropriate acid, usually in a stoichiometric ratio, in an aqueous, nonaqueous or partially aqueous medium as appropriate. The salts are recovered by filtration, by precipitation with a nonsolvent followed by filtration, by evaporation of the solvent, as appropriate, or, in the case of aqueous solutions, by lyophilization. Typical salts which may be prepared are those of hydrochloric acid, p-toluenesulfonic acid, fumaric acid, citric acid, succinic acid, salicydic acid, oxalic acid, hydrobromic acid, phosphoric acid, methanesulfonic acid, tartaric acid di-p-toluoyl tartaric acid, and mandelic acid.

The term "alkyl", as used herein, unless otherwise indicated, includes saturated monovalent hydrocarbon radicals having straight, branched or cyclic moieties or combinations thereof.

The compounds of the formula I and their pharmaceutically acceptable salts (hereafter "the active compounds") can be administered via either the oral, transdermal (e.g., through the use of a patch), intranasal, sublingual, rectal, parenteral or topical routes. Transdermal and oral administration are preferred. These compounds are, most desirably, administered in dosages ranging from about 0.25 mg up to about 1500 mg per day, preferably from about 0.25 to about 300 mg per day in single or divided doses, although variations will necessarily occur depending upon the weight and condition of the subject being treated and the particular route of administration chosen. However, a dosage level that is in the range of about 0.02 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds can be administered alone or in combination with pharmaceutically acceptable carriers or diluents by any of the several routes previously indicated.

More particularly, the active compounds can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of a similar type may also be employed as fillers in gelatin capsules; preferred materials in this connection also include lactose or milk sugar] as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active compound in either sesame or peanut oil or in aqueous propylene glycol can be employed. The aqueous solutions should be suitably buffered, if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active compounds topically when treating inflammatory conditions of the skin and this can be done by way of creams, jellies, gels, pastes, ointments and the like, in accordance with standard pharmaceutical practice Biological Assay The effectiveness of the active compounds in suppressing nicotine binding to specific receptor sites is determined by the following procedure which is a modification of the methods of Lippiello, P. M. and Fernandes, K. G. (in "The Binding of L-[$^3$H]Nicotine To A Single Class of High-Affinity Sites in Rat Brain Membranes", Molecular Pharm., 29, 448–54, (1986)) and Anderson, D. J. and Americ, S. P. (in "Nicotinic Receptor Binding of $^3$H-Cystisine, $^3$H-Nicotine and $^3$H-Methylcarmbamylcholine In Rat Brain", European J. Pharm., 253, 261–67 (1994)).

Procedure

Male Sprague-Dawley rats (200–300 g) from Charles River were housed in groups in hanging stainless steel wire cages and were maintained on a 12 hour light/dark cycle (7 a.m.–7 p.m. light period). They received standard Purina Rat Chow and water ad libitum.

The rats were killed by decapitation. Brains were removed immediately following decapitation. Membranes were prepared from brain tissue according to the methods of Lippiello and Fernandez (Molec Pharmacol, 29, 448–454, (1986) with some modifications. Whole brains were removed, rinsed with ice-cold buffer, and honogenized at 0° in 10 volumes of buffer (w/v) using a Brinkmann Polytron™, setting 6, for 30 seconds. The buffer consisted of 50 mM Tris HCl and had a pH of 7.5 at room temperature. The homogenate was sedimented by centrifugation (10 minutes; 50,000×g; 0 to 4° C. The supernatant was poured off and the membranes were gently resuspended with the Polytron and centrifuged again (10 minutes; 50,000×g; 0 to 4° C. After the second centrifugation, the membranes were resuspended in assay buffer at a concentration of 1.0 g/100 mL. The composition of the standard assay buffer was 50 mM Tris HCl, 120 mM NaCl, 5 mM KCl, 2 mM $MgCl_2$, 2 mM $CaCl_2$ and has a pH of 7.4 at room temperature.

Routine assays were performed in borosilicate glass test tubes. The assay mixture typically consisted of 0.9 mg of membrane protein in a final incubation volume of 1.0 mL. Three sets of tubes were prepared wherein the tubes in each set contained 50 mL of vehicle, blank, or test compound solution, respectively. To each tube was added 200 mL of [$^3$H]-nicotine in assay buffer followed by 750 mL of the membrane suspension. The final concentration of nicotine in each tube was 0.9 nM. The final concentration of cytisine in the blank was 1 mM. The vehicle consisted of deionized water containing 30 mL of 1 N acetic add per 50 mL of water. The test compounds and cytisine were dissolved in vehicle. Assays were initiated by vortexing after addition of the membrane suspension to the tube. The samples were incubated at 0 to 4° C. in an iced shaking water bath. Incubations were terminated by rapid filtration under vacuum through Whatman GF/B™ glass fiber filters using a Brandel™ multi-manifold tissue harvester. Following the initial filtration of the assay mixture, filters were washed two times with ice-cold assay buffer (5 m each). The filters were then placed in counting vials and mixed vigorously with 20 ml of Ready Safe™ (Beckman) before quantification of radioactivity. Samples were counted in a LKB Wallach Rackbeta™ liquid scintillation counter at 40–50% efficiency. All determinations were in triplicate.

Calculations

Specific binding IX to the membrane is the difference between total binding in the samples containing vehicle only and membrane VII and non-specific binding in the samples containing the membrane and cytisine VIII, i.e., Specific binding=IX=VII–VIII.

Specific binding in the presence of the test compound XI is the difference between the total binding in the presence of the test compound X and non-specific binding VIII, i.e., XI=X–VIII.

% Inhibition=(1–(XI/IX) times 100.

The compounds of the invention, which were tested, exhibited $IC_{50}$ values of less than 2 µM.

EXAMPLE 1

2Chloro-1-(6-chloro-1H-pyrrolo[2,3-b]Pyridin-3-yl)-ethanone. To a solution of 400 mg (2.62 mM) of 6-chloro-1H-pyrrolo[2,3-b]pyridine (Synthesis, 1992, 7, 661–663) dissolved in 15 mL of carbon disulfide was added 2.62 g of anhydrous aluminum chloride and 0.229 mL (2.88 mM) chloromethyl acetyl chloride. The reaction was refluxed for 2 hours. A second equivalent of chloromethyl acetyl chloride was added to the reaction and reflux continued for an additional 1 hour. The reaction mixture was cooled to room temperature and the carbon disulfide solvent decanted and discarded. The residue was cooled (ice bath) and the excess aluminum chloride decomposed by slow addition of water. The resulting mixture was mixed with an equal volume of ethyl acetate and the pH adjusted to 9.0 ($Na_2CO_3$). This mixture was filtered, and the ethyl acetate layer separated from the aqueous layer. The ethyl acetate layer was dried and evaporated. The residue was triturated with methyl isobutyl ketone and filtered to yield 200 mg product. NMR ($D_6$DMSO) δ12.82 (s, 1H), 8.62 (s, 1H), 8.5 (d, J=8.5 Hz, 1H), 7.32 (d, J=8.5 Hz, 1H), 4.92 (s, 2H). Mass spectrum m/e=229,231 (P+1; P+3). Rf (10:1 $CH_2Cl_2$: $CH_3OH$)=0.8.

EXAMPLE 2

1-(Chloro-1H-pyrrolo[2.3-b]pyridin-3-yl)-2-dimethylamino-ethanone. The title compound was prepared from 6-chloro-1H-pyrrolo[2,3-b]pyridine (*Synthesis*, 992, 7, 661–663) and dimethylaminoacetyl chloride hydrochloride (*Arch. Pharm.* 991, 324, 433–437) in a procedure similar to Example 1. NMR ($D_6$DMSO) δ8 12.65 (s, 1H), 8.60 (s, 1H), 7.95 (d, 1H), 7.32 (d, 1H), 3.60 (s, 2H), 2.22 (s, 3H). $^{13}$C NMR ($D_6$DMSO) 195.6, 147.5, 144.4, 134.8, 132.7, 118.0, 116.8, 114.0, 65.9, 45,4 (2). Mass spectrum: 237,239 (P+1, P+3).

EXAMPLE 3

6-Chloro-3-(2-chloro-ethyl)-1H-pyrrolo[2,3-b]pyridine. To a solution of 400 mg of 2-chlor-1-(6-chloro-1H-pyrrolo[2,3-b]pyridin-3-yl)-ethanone (1.75 mM) of in 2.80 mL of trifluroacetic acid was added 1.8 mL (12 mM) of triethylsilane and the mixture stirred at room temperature for 48 hours. The reaction mixture was diluted with 20 mL of ethyl acetate and the pH adjusted to 8.0 with addition of saturated $NaHCO_3$. The ethyl acetate layer was separated from the water layer, dried (MgSO4) and evaporated to yield 400 mg of a yellow solid residue. This residue was chromatographed on 25 grams of silica using 1:1 hexanes:ethyl acetate as the elutant. Appropriate fractions were combined to yield 350 mg of 6-Chloro-3-(2-chloro-ethyl)-1H-pyrrolo[2,3-b]pyridine as a white solid. NMR ($CDCl_3$) d 11.35 (s, 1H), 7.88 (d, J=8 Hz, 1H), 7.40 (s, 1H), 7.10 (d, J=8 Hz, 1H), 3.75 (t, J=6 Hz, 2H), 3.2 (t, J=6 Hz, 2H). $^{13}$C NMR ($CDCl_3$) 147, 129, 123, 118, 155 111, 44, 29. Mass spectrum: m/e=216, 218 (p+1, p+3).

EXAMPLE 4

[2-(6-Chloro-1H-pyrrolo[2,3-b]pyridin-3-yl)-ethyl]-dimethyl-amine. To a 25 mL saturated solution of dimethyl amine in ethanol was added 110 mg (0.51 mM) of 6-Chloro-3-(2-chloro-ethyl)-1H-pyrrolo[2,3-b]pyridine and 76 mg (0.506 mM) of sodium iodide. The mixture was heated to 90° C. in a steel bomb for 2 hours. After cooling to room temperature, an additional 15 mL of ethanol saturated with dimethyl amine was added, and the bomb heated to 90° C. for 14 hours. The reaction mixture was cooled to room temperature and the ethanol evaporated. The residue was mixed with 25 mL of water, the pH adjusted to 9 and the mixture extracted with ethyl acetate. The ethyl acetate was dried and evaporated to yield 115 mg of an oil. The oil was triturated with hexanes to yield a white solid. NMR ($CDCl_3$) δ10.37 (s, 1H), 7.85 (d, 1H), 7.16 (s, 1H), 7.05 (d, 1H), 2.95 (t, 2H), 2.62 (t, 2H), 2.32 (s, 6H). $^{13}$C NMR ($CDCl_3$) 147.9, 143.7, 129.7, 122.7, 118.9, 114.9, 133.0, 60.1, 45.5 (2), 23.9. Mass spectrum: m/e=224, 226 (P+1, P=3). The above material was dissolved in 10 mL of ethyl acetate and reacted with 10 mL of ethyl acetate saturated with HCl. The resulting precipitate was filtered and dried to yield [2-(6-Chloro-1H-pyrrolo[2,3-b]pyridin-3-yl)-ethyl]-dimethyl-amine hydrochloride.

EXAMPLE 5

6-Chloro-3-(2-iodo-ethyl)-1H-pyrrolo[2,3-b]pyridine. A mixture of 800 mg (3.72 mM) of 6-Chloro-3-(2-chloro-ethyl)-1H-pyrrolo[2,3-b]pyridine and 1.67 g (11.2 mM) of NaI was refluxed in 150 mL of acetone for 12 hours. The reaction mixture was cooled to room termperature and the acetone evaporated. The residue was treated with saturated $NaHCO_3$ and extracted with ethyl acetate. The ethyl acetate extracts were combined, dried with $Na_2SO_4$ and evaporated to yield 1.0 g of a pale yellow solid. This solid (approximately 80% 6-Chloro-3-(2-iodo-ethyl)-1H-pyrrolo [2,3-b]pyridine and 20% 6-Chloro-3-(2-chloro-ethyl)-1H-pyrrolo[2,3-b]pyridine was used in subsequent reactions without further purification. NMR ($CDCl_3$) δ11.3 (s, 1H), 7.8 (d, 1H), 7.2 (s, 1H), 7.1 (d, 1H), 3.42 (t, 2H), 3.35 (t, 2H). Mass spectrum: 307,309 (P=1, P+3).

EXAMPLE 6

[2-(6-Chloro-1H-pyrrolo[2,3-b]pyridin-3-yl)-ethyl]-methyl-amine. A mixture of 1 g (3.26 mM) of 6-Chloro-3-(2-iodo-ethyl)-1H-pyrrolo[2,3-b]pyridine and 0.49 g (3.26 mM) NaI were mixed together in 100 mL of an ethanol solution saturated with methyl amine gas. This solution was heated to 100° C. in a steel bomb for 12 hours. The reaction mixture was cooled to room temperature and the solvent evaporated. The residue was chromatographed on silica using a mixture of 10:1 $CH_2Cl_6$: $CH_3OH$ as the elutant. The appropriate fractions were combined and evaporated. The residue was crystallized from isopropyl ether-methanol to yield 140 mg of [2-(6-Chloro-1H-pyrrolo[2,3-b]pyridin-3-yl)-ethyl]-methyl-amine. MP=214–215° C. NMR ($D_6$ DMSO) δ11.75 (s, 1H), 8.08 (d, 1H), 7.41 (s, 1H), 7.15 (d, 1H), 3.20 (t, 2H), 3.02 (t, 2H), 2.60 (s, 3H). $^{13}$C NMR ($D_6$ DMSO) 147.5, 143.2, 129.9, 124.8, 118.2, 114.8, 108.7, 48.4, 32.6, 21.6. Mass spectrum: m/e=210, 212(P+1, P+3).

EXAMPLE 7

4-Nitro-5-(1H-pyrrolo[2,3-b]pyridin-3-yl)-pent-4-enoic acid methyl ester. A mixture of 1.47 g (10 mM) of 1H-Pyrrolo[2,3-b]pyridine-3-carbaldehyde (*J. Am. Chem. Soc.*, 1955, 77, 457–459), 77 mg (10 mM) of ammonium acetate and 2.55 mL (20 mM) of methyl 4-nitrobutyrate (Aldrich) was refluxed in 10 mL of THF for 1 hour. An additional 500 mg of ammonium acetate was added and the mixture refluxed for an additional 3 hours. The reaction was cooled to room temperature, the solvent evaporated, and the residue chromatographed on silica using ethyl acetate as the elutant. Appropriate fractions were combined to yield 410 mg of the desired product as an oil. NMR ($D_6$ DMSO) δ12.80 (s, 1H), 8.42 (s, 1H), 8.37 (m, 2H), 8.18 (s, 1H), 7.25 (m, 1H), 3.62 (s, 3H), 3.25 (t, 2H), 2.68 (t, 2H). $^{13}$C NMR ($D_6$ DMSO) 172.4, 148.7, 144.5, 144.4, 130.0, 127.3, 126.9, 119.9, 117.3, 106.1, 51.6, 30.5, 23.6. Mass Spectrum: m/e= 276 (P+1).

EXAMPLE 8

4-Nitro-5-(1H-pyrrolo[2,3-b]pyridin-3-yl)-pentanoic acid methyl ester. To a suspension of 0.124 g (0.45 mM) of 4-Nitro-5-(1H-pyrrolo[2,3-b]pyridin-3-yl)pent-4-enoic acid methyl ester in 8 mL of methanol was added 125 mg (3.3 mM) of sodium borohydride, the reaction mixture was stirred at room temperature for 1 hour. An additional 100 mg of sodium borohydride was added and the mixture was stirred for an additional 1 hour. To this mixture was added 1 mL of acetic acid. The reaction solvent was evaporated and the residue was dissolved in ethyl acetate and treated with saturated sodium bicarbonate. The ethyl acetate layer was removed form the aqueous layer, dried and evaporated to yield 130 mg of product. TLC (10:1 $CHCl_3$, $CH_3OH$) Rf=0.35. NMR ($CDCl_3$) δ11.8 (s, 1H), 8.35 (d, 1H), 7.90 (d, 1H), 7.25 (s, 1H), 7.10 (dd, 1H), 4.90 (m, 1H), 3.65 (s, 3H), 3.45 (dd, 1H), 3.20 (dd, 1H), 2.1–2.5 (m, 4H). $^{13}C$ NMR ($CDCl_3$) 172.3, 148.8, 142.6, 127.0, 124.2, 119.8, 115.7, 107.6, 80.0, 51.9, 30.2, 29.9, 28.3. Mass Spectrum: m/e=278 (p+1).

EXAMPLE 9

4-Amino-5-(1H-pyrrolo[2,3-b]pyridin-3-yl)-pentanoic acid methyl ester. To a solution of 165 mg (0.595 mM) of 4-Nitro-5-(1H-pyrrolo[2,3-b]pyridin-3-yl)-pentanoic acid methyl ester in 15 mL of acetic add was added 450 mg (0.595 mM) of ammonium acetate and approximately 100 mg of Raney nickel. The mixture was hydrogenated at 50 psi for 12 hours. The mixture was filtered and the solvent evaporated. The residue was treated with an equal volume of ethyl acetate and saturated sodium bicarbonate. The ethyl acetate layer was dried and evaporated to yield 85 mg of product which was used in the next synthetic step without further purification. TLC: (10:1 $CHCl_3$: $CH_3OH$) Rf=0.1 Mass Spectrum: m/e=248 (P+1).

EXAMPLE 10

5-(1H-Pyrrolo[2,3-b]pyridin-3-ylmethyl)-pyrrolidin-2-one. A solution of 2.5 g (0.10.1 mM) of 4-Amino-5-(1H-pyrrolo[2,3-b]pyridin-3-yl)-pentanoic acid methyl ester was dissolved in 20 mL of ethyl acetate. To this solution was added 20 mL of 1N sodium carbonate, and the mixture was stirred at room temperature for 6 hours. The ethyl acetate layer was dried and evaporated. The residue was chromatographed on silica using 95:5 $CHCl_3$:$CH_3OH$ to yield 1.48 g of product as a white crystalline solid. MP=160–162° C. NMR ($CDCl_3$) δ11.4 (s, 1H), 8.05 (m, 1H), 7.85 (d, 1H), 7.45 (s, 1H), 7.18 (s, 1H), 6.95 (m, 1H), 4.0 (m, 1H), 2.8–3.0 (m, 2H), 2.2–2.4 (m, 3H), 1.85 (m, 1H). $^{13}C$ NMR ($CDCl_3$) 178.6,148.9, 142.4, 127.0, 123.6, 120.1, 115.3, 109.8, 55.2, 32.6, 30.3, 26.8. Mass Spectrum: m/e=216 (p+1).

EXAMPLE 11

3-Pyrrolidin-2-ylmethyl-1H-pyrrolo[2,3-b]pyridine. A mixture of 313 mg (1.46 mM) of 5-(1H-Pyrrolo[2,3-b]pyridin-3ylmethyl)-pyrrolidin-2-one and 170 mg (4.47 mM) of lithium aluminum hydride was refluxed in 10 mL of dioxane for 5 hours. The solution was cooled to room temperature and the excess lithium aluminum hydride decomposed with 1 mL of saturate NaCl. To this mixture was added 300 mL of ethyl acetate, and 15 g of anhydrous $Na_2SO_4$. The reaction mixture was filtered, and evaporated to yield 254 mg of the amine as a dark oil, this material was used directly in the next synthetic step. Mass spectrum: m/e=202(p=1).

EXAMPLE 12

2-(1H-Pyrrolo[2,3-b]pyridin-3-ylmethyl)-pyrrolidine-1-carboxylic acid tert-butyl ester. A mixture of 254 mg (1.26 mM) of 3-Pyrrolidin-2-ylmethyl-1H-pyrrolo[2,3-b]pyridine and 302 mg (1.38 mM) of di-tert-butyl-dicarbonate (Aldrich) in 10 mL of dioxane was stirred at room temperature for 12 hours. TLC (10:1 CHCl3:CH3OH) indicated new product formation, and mass spectrum indicated m/e=302 (p+1). This solution was used directly in the next synthetic step.

EXAMPLE 13

3-(1-Methyl-pyrrolidin-2-ylmethyl)-1H-pyrrolo[2,3-b] pyridine. To the above dioxane solution was added 177 mg (4.65 mM) of lithium aluminum hydride. The mixture was refluxed for 6 hours. The reaction mixture was cooled to room temperature, and the excess lithium aluminum hydride decomposed by addition of 1 mL of saturated NaCl. The mixture was poured into 300 mL of ethyl acetate, and the solution dried with 20 g of anhydrous $Na_2SO_4$. The mixture was filtered and evaporated. The residue was chromatographed on 10 g of deactivated silica (500 g silica slurried for 1 h in 2 L of 4% $KH_2PO_4$, and dried at 120° C.) to yield 125 mg of product as an oil. NMR ($CDCl_3$) δ11.4 (s, 1H), 8.3 (m, 1H), 7.95 (d, 1H), 7.18 (s, 1H), 7.08 (m, 1H), 3.15 (m, 2H), 2.6 (m, 1H), 2.45 (s, 3H), 2.43 (m, 1H), 2.20 (m, 1H), 1.8 (m, 2H), 1.6 (m, 2H). $^3C$ NMR ($CDCl_3$) 149.1, 142.3, 127.4, 122.8, 120.6, 115.1, 112.3, 66.8, 57.5, 40.8, 31.4, 30.1, 21.8. Mass spectrum: m/e=216 (p+1). TLC (10:1 $CHCl_3$:$CH_3OH$): Rf=0.1.

EXAMPLE 14

*J. Het. Chem.* 1984, 21,421–3

3-(2-Iodo-ethyl)1H-pyrrolo[2,3-b]pyridine. To a solution of 7.0 g (38.8 mM) of 3-(2-Chlor-ethyl)-1H-pyrrolo[2,3-b] pyridine in 250 mL of acetone was added 17.5 g (116 mM) of NaI, and the mixture heated to reflux for 48 hours. The reaction was cooled to room temperature, filtered, and the solvent evaporated. The residue was dissolved in 100 mL of ethyl acetate and water, and the pH adjusted to 10 with 1N NaOH. The ethyl acetate layer was dried and evaporated to yield 10.1 g of product as a yellow solid. NMR ($CDCl_3$) δ11.6 (s, 1H), 8.32 (d, 1H), 7.92 (d, 1H), 7.29 (s, 1H), 7.08 (m, 1H), 3.40 (m, 2H), 3.32 (m, 1H). $^3C$ NMR ($CDCl_3$) 149, 142.5, 127.1, 123.0, 119.7, 115.4, 113.6, 30.3, 5.8. Mass spectrum: m/e=273 (p+1).

EXAMPLE 15

Dimethyl-[2-(1H-pyrrolo[2,3-b]pyridin-3-yl)ethyl]-amine. A solution of 544 mg (2.0 mM) of 3-(2-lodo-ethyl)-1H-pyrrolo[2,3-b]pyridine was dissolved in 100 mL of ethanol which had been saturated with dimethylamine gas. This solution was placed in a steel bomb and heated to 100° C. for three hours. The reaction was cooled to room temperature and the solvent evaporated to yield 300 mg of product as a yellow amorphous solid. NMR ($CDCl_3$) δ11.9 (s, 1H), 8.28 (d, 1H), 7.90 (d, 1H), 7.15 (s, 1H), 7.02 (m, 1H), 2.92 (t, 2H), 2.60 (t, 2H), 2.30 (s, 6H). $^{13}C$ NMR ($CDCl_3$) 149.2, 142.1, 127.2, 122.6, 120.3, 114.9, 112.3, 60.3, 45.4 (2), 42.3, 23.9. Mass spectrum: m/e=190 (p+1).

EXAMPLE 16

Methyl-[2-(1H-pyrrolo[2,3-b]pyridin-3-yl)-ethyl]-amine. This was prepared as described in the above example using a saturated solution of ethanol with methylamine gas. NMR ($CDCl_3$) δ11.3 (s, 1H), 8.3 (m, 1H), 7.9 (d, 1H), 7.15 (s, 1H), 7.0 (m, 1H), 2.9 (m, 4H), 2.42 (s, 3H). $^{13}C$ NMR ($CDCl_3$) 149.2, 142.4, 127.3, 122.8, 120.2, 115.1, 112.2, 52.1, 36.3, 25.7. Mass spectrum: m/e=176 (p+1).

EXAMPLE 17

2-(1H-Pyrrolo[2,3-b]pyridin-3-yl)-ethylamine. This was prepared as described in the above example using a saturated solution of ethanol with ammonia. Mass Spectrum: m/e=162 (p+1). This compound is a known compound (*J. Am. Chem. Soc.* 1956, 78, 1247, U.S. Pat. No. 3,362,956).

EXAMPLE 18

3-(2-Piperidin-1-yl-ethyl)-1H-pyrrolo[2,3-b]pyridine. A solution of 100 mg (0.37 mM) of 3-(2-Iodo-ethyl)-1H-pyrrolo[2,3-b]pyridine and 0.1 mL (1.0 mM) of piperidine in 1.0 mL of ethanol was refluxed for 12 hours. The reaction was cooled to room temperature, and added to 50 mL of an ethyl acetate-water mixture. The pH was adjusted to 9.0 with 1N NaOH and the ethyl acetate layer dried and evaporated to yield 80 mg of product as a yellow solid. NMR (CDCl$_3$) δ10.9 (s, 1H), 8.3 (d, 1H), 7.9 (d, 1H), 7.15 (s, 1H), 7.0 (m, 1H), 2.9 (t, 2H), 2.6 (t, 2H), 2.5 (m, 4H), 1.7 (m, 4H), 1.4 (m, 2H). $^{13}$C NMR (CDCl$_3$) 149.2, 142.4, 127.3, 122.2, 120.3, 115.1, 112.9, 60.0, 54.6 (2), 25.9 (2), 24.4, 23.0. Mass spectrum: m/e=230 (p+1).

I claim:

1. A method for treating a disease or condition of the brain associated with depletion of nicotine receptors in a patient in need thereof comprising administering to said patient an effective amount of a compound of the formula

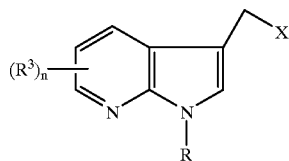

(I)

wherein X is:

a) —CH$_2$NR$^1$R$^2$, b)
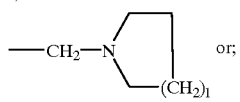

or;

c)
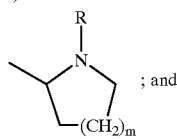

; and

R, R$^1$ and R$^2$ are independently selected from hydrogen and C$_1$–C$_6$ alkyl;
R$^3$ is selected from hydrogen, halogen and C$_1$–C$_6$ alkyl.
l is an integer from 0–4;
m is an integer from 0–4; and
n is an integer from 0–2; or a pharmaceutically acceptable salt thereof.

2. The method of claim 1 wherein said condition of the brain is nicotine addiction.

3. A compound of the formula

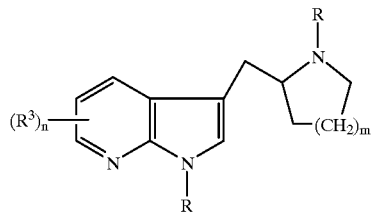

wherein R is selected from hydrogen and C$_1$–C$_6$ alkyl;
R$^3$ is selected from hydrogen, halogen and C$_1$–C$_6$ alkyl;
m is an integer from 0–4; and
n is an integer from 0–2; or a pharmaceutically acceptable salt thereof.

4. A compound of the formula

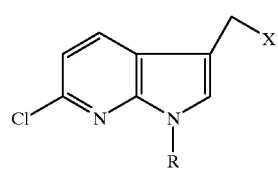

wherein X is

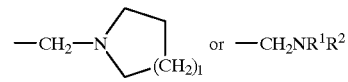

R, R$^1$ and R$^2$ are independently selected from hydrogen and C$_1$–C$_6$ alkyl;
l is an integer from 0–4; or a pharmaceutically acceptable salt thereof.

5. The compound of claim 4 wherein X is —CH$_2$NR$^1$R$^2$; R$^1$ and R$^2$ are methyl;
and R is H.

6. The compound of claim 4 wherein X is

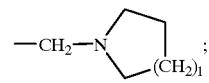

;

l is 1; and R is H.

* * * * *